United States Patent [19]

Garver, Sr.

[11] 4,403,990

[45] Sep. 13, 1983

[54] SUPPORT ASSEMBLY FOR A CANNULA AND THE LIKE

[75] Inventor: Edward B. Garver, Sr., Lindenhurst, Ill.

[73] Assignee: Baxter Travenol Laboratories, Inc., Deerfield, Ill.

[21] Appl. No.: 326,736

[22] Filed: Dec. 2, 1981

[51] Int. Cl.$^3$ .............................................. A61M 5/00
[52] U.S. Cl. .................................. 604/273; 604/117; 156/294
[58] Field of Search ............................... 604/272–274, 604/283, 117, 411, 192, 263; 156/428, 294

[56] References Cited

U.S. PATENT DOCUMENTS

| | | |
|---|---|---|
| 2,949,913 | 8/1960 | Gewecke et al. . |
| 3,243,211 | 3/1966 | Wetmore . |
| 3,381,057 | 4/1968 | Tadao Senoo et al. . |
| 3,382,121 | 5/1968 | Sherlock . |
| 3,433,687 | 3/1969 | Price . |
| 3,525,799 | 8/1970 | Ellis . |
| 3,565,852 | 2/1971 | Conix et al. . |
| 3,567,799 | 3/1971 | Prevorsek . |
| 3,576,387 | 4/1971 | Derby . |
| 3,582,457 | 6/1971 | Barthell . |
| 3,597,372 | 8/1971 | Cook . |
| 3,629,366 | 12/1971 | Brinkman . |
| 3,629,424 | 2/1972 | Gray et al. . |
| 3,651,172 | 3/1972 | Barkey et al. . |
| 3,652,714 | 3/1972 | Berger . |
| 3,669,824 | 6/1972 | Hess . |
| 3,697,624 | 10/1972 | Braunstein . |
| 3,699,082 | 10/1972 | Koerner et al. . |
| 3,708,611 | 1/1973 | Dinger . |
| 3,717,717 | 2/1973 | Cunningham et al. . |
| 3,723,572 | 3/1973 | Reese et al. . |
| 3,835,089 | 9/1974 | Fox et al. . |
| 3,883,611 | 5/1975 | Nelson . |
| 3,904,707 | 9/1975 | Gebhart et al. . |
| 3,907,926 | 9/1975 | Brown et al. . |
| 3,917,743 | 11/1975 | Schroeder et al. . |
| 3,946,091 | 3/1976 | Sakata et al. . |
| 3,953,394 | 4/1976 | Fox et al. . |
| 3,959,200 | 5/1976 | Scott . |
| 3,962,368 | 6/1976 | Herwig et al. . |
| 3,976,529 | 8/1976 | Weischselbaum . |
| 3,988,387 | 10/1976 | Chimura et al. . |
| 4,011,285 | 3/1977 | Seymour et al. . |
| 4,011,286 | 3/1977 | Seymour et al. . |
| 4,024,008 | 5/1977 | Gregornik et al. . |
| 4,035,534 | 7/1977 | Nyberg . |
| 4,048,255 | 9/1977 | Hillier et al. . |
| 4,069,278 | 1/1978 | Borman et al. . |
| 4,070,044 | 1/1978 | Carrow . |
| 4,070,417 | 1/1978 | Isaka . |
| 4,075,262 | 2/1978 | Schaefgen . |
| 4,092,193 | 5/1978 | Brooks . |
| 4,115,333 | 9/1978 | Phipps, Jr. et al. . |
| 4,116,925 | 9/1978 | Brachman et al. . |
| 4,131,595 | 12/1978 | Breitenfellner et al. . |
| 4,131,714 | 12/1978 | Karkoski . |
| 4,138,374 | 2/1979 | Currie . |
| 4,143,093 | 3/1979 | Ruter . |
| 4,152,511 | 5/1979 | Bier et al. . |
| 4,161,579 | 7/1979 | Edelman et al. . |
| 4,167,541 | 9/1979 | Alexander . |
| 4,185,046 | 1/1980 | Pengilly et al. . |
| 4,207,364 | 6/1980 | Nyberg . |
| 4,210,479 | 7/1980 | Fabisiewicz . |
| 4,211,689 | 7/1980 | Borman . |
| 4,212,791 | 7/1980 | Avery . |
| 4,234,708 | 11/1980 | Edelman et al. . |
| 4,239,677 | 12/1980 | Dieck . |
| 4,243,712 | 1/1981 | Hoheisel et al. . |
| 4,246,381 | 1/1981 | Robeson . |
| 4,251,310 | 2/1981 | Goldhaber et al. . |
| 4,254,243 | 3/1981 | Keck . |
| 4,258,478 | 3/1981 | Jackson, Jr. et al. . |
| 4,259,458 | 3/1981 | Robeson . |
| 4,286,011 | 8/1981 | Wong . |
| 4,287,325 | 9/1981 | Jackson, Jr. et al. . |

FOREIGN PATENT DOCUMENTS

46727A/26 of 0000 Japan .

OTHER PUBLICATIONS

Modern Plastics Encyclopedia, (1979–1980), vol. 56, No. 10A, pp. 49 through 58, (a MacGraw–Hill publication).

Primary Examiner—Stephen C. Pellegrino
Attorney, Agent, or Firm—Paul C. Flattery; Daniel D. Ryan

[57] ABSTRACT

An assembly is provided which is attachable to a member, such as a cannula, in a uniformly secure fashion in response to heat. The assembly includes a first portion, which is deformable in the presence of heat and into which the member can be slidably inserted, and a second portion, which is disposed about the first portion in an interference fit so as to exert a force inwardly upon the first portion in the direction of the member therein confined. When the member is heated, the first portion becomes deformable, and the force exerted by the second portion serves to constrict the first portion into a tight conformance fit about the member. The member is thereby secured to the assembly. In the preferred embodiment, the first portion is made of an autoclavable thermoplastic polyester whose bonding characteristics are enhanced by the addition of a nonautoclavable copolyester of superior bonding strength. The second portion is preferably an autoclavable elastomer.

6 Claims, 5 Drawing Figures

SUPPORT ASSEMBLY FOR A CANNULA AND THE LIKE

TECHNICAL FIELD OF THE INVENTION

The invention generally relates to the assembly of fabricated parts, and, in particular, to the utilization of heat to secure these parts together.

The invention also relates to support hub assemblies for cannulas and the like, as well as to the utilization of heat to secure the cannulas to such assemblies.

DESCRIPTION OF THE PRIOR ART

In the field of medical products, there is a need to attach cannulas, such as catheters, hypodermic needles, and phlebotomy needles, to support hub assemblies. These cannulas are typically made of stainless steel, and the associated hub assemblies are typically made of plastic.

It is crucial that the cannula be securely attached to the hub assembly. Movement of the cannula within the confines of the hub assembly, or actual separation of the cannula from the hub assembly itself, must be avoided. Furthermore, the interface between the cannula and the hub assembly must be as fluid-tight as possible to avoid leakage of blood or other parenteral fluids about the portion of the needle confined by the hub assembly.

Various methods for securing a cannula to a hub assembly exist. For example, as discussed in the following documents, the hub assembly can be injection molded about the cannula:

Walter—U.S. Pat. No. 2,702,037
Brookfield—U.S. Pat. No. 3,294,089
Hennig—United Kingdom Specification No. 810,860

Another known method is to use adhesives or epoxies to chemically bond the cannula to the hub assembly. This method is discussed in the following U.S. patents:

Gewecke—U.S. Pat. No. 3,096,763
McConnaughey et al.—U.S. Pat. No. 3,096,763
Santomieri—U.S. Pat. No. 3,330,278
Pagones et al.—U.S. Pat. No. 3,523,530
Geiger—U.S. Pat. No. 4,121,588

In this regard, the Examiner's attention is also directed to the copending U.S. Patent Application of Emil Soika entitled CANNULA SUPPORT ASSEMBLY AND ITS METHOD OF MANUFACTURE, Ser. No. 326,739 as well as to the copending U.S. Patent Application of Edward Garver et al entitled TAMPER-PROOF CANNULA SUPPORT ASSEMBLY, Ser. No. 326,737. Both of these copending applications share the same filing date and assignee as this application.

Still another known method is to secure the cannula to the hub assembly by swagging or crimping. This method is discussed in Stevens et al, U.S. Pat. No. R. 28,713.

The use of heat, such as that generated by conduction, electromagnetic, or resistance heating methods, in the assembly of fabricated parts is also known. The use of heat readily lends itself to less labor-intensive and, hence, more cost effective production techniques and can result in bonds which meet high performance requirements. The use of heat to secure the cannula to the hub assembly can thus represent a desirable alternative to the methods heretofore discussed.

It is thus one of the principal objects of this invention to provide for the assembly of fabricated parts utilizing heat in a manner which meets the high performance requirements surrounding the attachment of cannulas to support hub assemblies and which readily lends itself to large scale, automated production techniques.

SUMMARY OF THE INVENTION

To achieve this and other objects, the invention provides an assembly which is attachable to a member, such as a cannula, in a uniformly secure fashion and in a manner which lends itself to large scale, automated production techniques.

The assembly generally comprises first means which receives the member to be attached. The first means is operative for assuming a deformable state in the presence of heat. The assembly also includes second means which is disposed about the first means. The second means is operative, when the first means is in its deformable state, for constricting the first means into a conformance fit about the member. A uniformly secure connection between the assembly and the member results.

In one embodiment, the assembly includes plastic materials. More particularly, the first means includes a thermoplastic element which is open to receive the member. The second means includes an elastomeric element which peripherably surrounds the thermoplastic element and exerts a force inwardly upon the thermoplastic element. When the member which is disposed within the thermoplastic element is heated, such as by an electromagnetic heating process, the thermoplastic element softens, and the force exerted by the elastomeric element acts to constrict the thermoplastic element into a tight conformance fit about the member. This conformance fit secures the member within the thermoplastic element, and thus to the assembly itself.

In the preferred embodiment, the thermoplastic element is made of a material which is also heat bondable to the member which is to be supported. This serves to further strengthen the connection between the member and the thermoplastic element.

The assembly is ideally suited for use in the medical field, and, in particular, for supporting metallic members, such as stainless steel cannulas. In this embodiment, the materials from which the thermoplastic element and the elastomeric element are fabricated are preferably preselected so that the resulting assembly is autoclavable. Furthermore, the material selected for the thermoplastic element is preferably not only heat bondable to the stainless steel of the cannula, but is also solvent bondable to tubing made of medical grade polyvinyl chloride plastic.

To optimize the above preferred performance requirements, a preferred polyester material for the thermoplastic element is disclosed in copending U.S. Patent Application of Edward Garver entitled AN AUTOCLAVABLE THERMOPLASTIC MATERIAL WHICH IS HEAT BONDABLE TO A CANNULA AND THE LIKE Ser. No. 326,738. This copending application shares the same filing date ans assignee as this application.

The invention also provides a method for assembling fabricated parts utilizing heat. The method is ideally suited to automation and meets the cost demands of mass production.

Other features and advantages of the embodiments of the invention will become apparent upon reviewing the following more detailed description, the drawings, and the appended claims.

Figure 1:
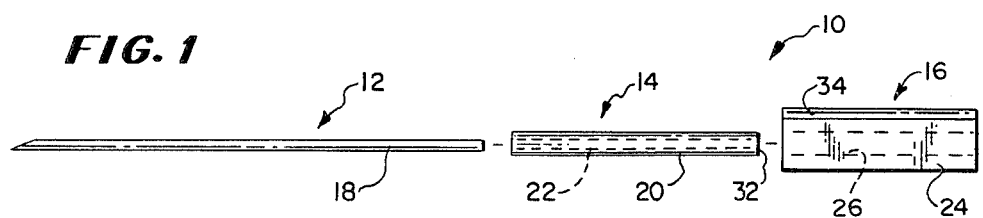
FIG. 1 is an exploded view of a support assembly which is attachable to a cannula and the like and which embodies various of the features of the invention.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it it to be understood that the phraseology and terminology employed herein is for the purpose of description and should not be regarded as limiting.

DESCRIPTION OF THE PREFERRED EMBODIMENTS

Shown in the drawings is an assembly 10 which is attachable to a member 12 in response to heat.

As is shown in FIG. 1, the assembly 10 includes a first portion or element 14, into which the member 12 can be inserted (see also FIGS. 2 and 4), and a second portion 16, into which the first portion 14 can be inserted. The first portion 14 is operative for assuming a deformable state in the presence of heat, and the second portion 16 is operative, when the first member 14 is in this deformable state, for constricting the first portion 14 into a conformance fit about the member 12. The resulting conformance fit is shown in FIGS. 3 and 5.

The first and second portions 14 and 16 of the assembly 10 can be fabricated utilizing various materials. However, the assembly 10 is particularly well suited to the utilization of plastic materials. For this reason, the illustrated and preferred embodiment contemplates this construction.

In this embodiment, the first portion 14 is made of a thermoplastic material. By "thermoplastic", it is meant that the material of the first member 14 has the property of softening and becoming deformable in the presence of a given amount of heat (hereinafter referred to as its "softening point") and of hardening again when cooled.

In this respect, the first member 14 may be fabricated virtually of any amorphous or semicrystalline thermoplastic material which is compatible with the material from which the associated member 12 is fabricated.

Also in this arrangement, the second portion 16 is preferably made of an elastomeric material. By "elastomeric", it is meant that the material of the second member 16 has "rubber-like" qualities and an interior resilience by virtue of which the member 16 resiliently resists and recovers from deformation.

The second portion 16 may be fabricated of virtually any elastomeric plastic. Alternately, natural or manmade rubber may be utilized. The interior resilience of the portion 16 must be sufficient to overcome the elastic memory of the associated thermoplastic portion 14, as well as sufficient to constrict the associated portion 14 into the desired conformance fit configuration.

Figure 2:
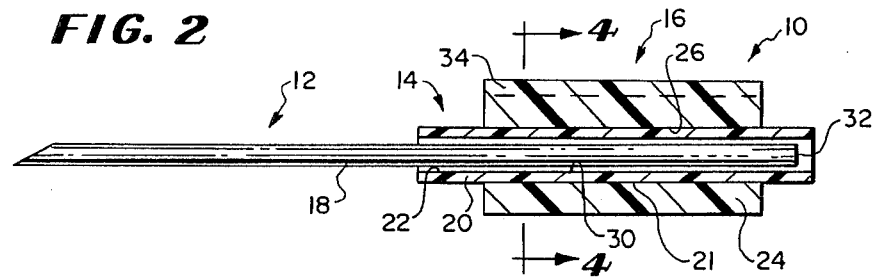
FIG. 2 is an assembled section view of the support assembly shown in FIG. 1 before the cannula is secured thereto.
Figure 3:
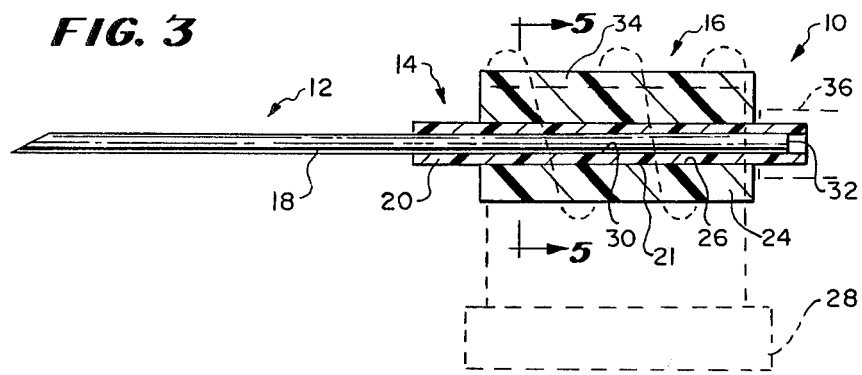
FIG. 3 is an assembled section view of the cannula support assembly shown in FIG. 1 after the cannula is secured thereto utilizing electromagnetic heating.
Figure 4:
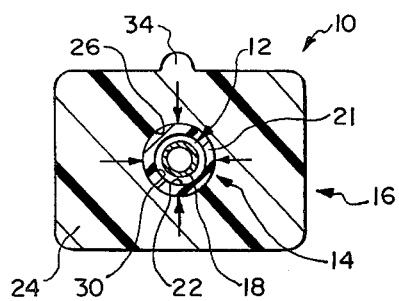
FIG. 4 is a end section view of the cannula support assembly taken generally along line 4—4 in FIG. 2.
Figure 5:
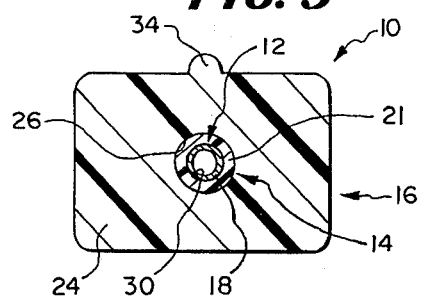
FIG. 5 is an end section view of the cannula support assembly taken generally along line 5—5 in FIG. 3.

As can be seen in FIGS. 2 and 4, the first portion 14 is internally configured with respect to the member 12 to normally accommodate the selective positioning of the member 12 within its confines. More particularly, and as is shown in FIG. 4, the normal interior dimensions of the first portion 14 exceeds the exterior dimensions of the member 12 by a measurable amount. As a result, the member 12 is received by the first portion 14 of the assembly in a slide-fit or slip-fit fashion.

As can also be seen in FIGS. 2 and 4, the first and second portions 14 and 16 are respectively configured to achieve an interference fit of the first portion 14 within the second portion 16. More particularly, the exteral dimensions of the first portion 14 exceeds the interior dimensions of the elastomeric second portion 16 by a measurable amount.

The particular size and configuration of the thermoplastic and elastomeric portions 14 and 16 of the assembly 10 can vary according to the size and configuration of the member 12, as well as the particular operative demands of the contemplated use. While the assembly 10 is applicable for use in a diverse number of operative environments, the illustrated embodiment specifically envisons use of the assembly 10 as a plastic support hub for a cannula, such as a catheter, hypodermic needle, or phlebotomy needle.

In the context of the illustrated use, the member 12 takes the form of a phlebotomy needle 18. Accordingly, the thermoplastic first portion 14 takes the form of a member 20 having an interior configuration which normally slidingly receives the needle 18. To correspond to the elongated tubular configuration of the needle 18, the member 20 is also generally elongated and tubular in shape, having a bore 22 (see FIGS. 2) and 4) which extends along its axial length and which constitutes its normal internal configuration heretofore described.

As can be seen in FIG. 2 and 4, the interior diameter of the bore 22 exceeds the exterior diameter of the needle 18. The bore 22, then, normally accommodates the shank of the needle 18 in the heretofore described slidefit fashion. The operative, or beveled, end of the needle 18 is thereby disposed in an outwardly projecting, exposed position beyond one end of the member 20.

In this particular arrangement, and as can be seen in FIGS. 2 and 4, the elastomeric second portion 16 takes the form of a member 24 having an interior configuration which receives the thermoplastic member 20 in an interference fit relationship. While the elastomeric member 24 may be variously constructed and configured to so conform to the exterior dimensions of the thermoplastic member 20, in the illustrated embodiment, the elastomeric member 24, like the thermoplastic member 20, is generally elongated and tubular in shape and has an axially extending bore 26. The interior diameter of the elastomeric member bore 26 is measurably less than the exterior diameter of the thermoplastic member 20. The thermoplastic member 20 is thus received in the desired interference fit relationship within the bore 26.

As generally shown by arrows in FIG. 4, the internal resiliency of the elastomeric member 24 exerts a uniform compression force radially inwardly upon the periphery of the portion 21 of the thermoplastic member 20 which is subject to the interference fit. This force tightly secures the thermoplastic member 20 against rotational and lateral movement within the elastomeric member bore 26 without the use of solvents or other bonds.

This same force also serves to secure the needle 18 within the thermoplastic member bore 22 with the thermoplastic member 22 is exposed to heat.

More particularly, by using an electromagnetic heating unit 28 (shown in phantom lines in FIG. 3), the needle 18 is heated along its axial length. The heat emanating from the needle 18 will elevate the temperature within the confines of the bore 22. When the temperature within the bore 22 reaches the softening point of the thermoplastic member 20, the member 20, because of its thermoplastic properties, softens and becomes deformable.

When the thermoplastic member 20 is in this softened or deformable state, the force exerted by the elastomeric member 24 upon the thermoplastic member portion 21 serves to uniformly constrict the normal interior configuration of the bore 22 (as shown in FIGS. 2 and 4) radially inwardly toward the needle 18, until a conformance fit configuration is achieved about the needle 18 (as shown in FIGS. 2 and 5).

Preferably, the material from which the thermoplastic member 20 is made is also thermally fusable or bondable to the material of the needle 18. Thus, as the member 20 is constricted into its conformance fit configuration about the needle 18, the heat emanating from the needle 18 will also serve to bond the member portion 21 to the needle 18 along the interface between the needle 18 and the interior sidewall 30 of the bore 22.

The needle 18 can be metallic in nature, such as stainless steel, but it may also be fabricated from a plastic which is approved for blood contact and which is thermosetting or which does not otherwise melt or structurally deform at the softening point temperature of the associated thermoplastic member 20, or, in the preferred embodiment, at the temperature at which the bond between the needle 18 and the member 20 occurs.

As can be seen in FIGS. 2 and 3, the shank end 32 of the needle 12 is preferably disposed closely adjacent to the terminus of the thermoplastic member 20. The needle 18 thus provides interior rigidity and support virtually along the entire length of the thermoplastic member 20. The shank end 32 is also readily accessible should other methods be utilized to heat the needle 18, such as electrical resistance or conduction techniques which require contact with both ends of the needle 18.

In the particular operative embodiment of the illustrated embodiment, it is of course desirable that the entire hub assembly 10 be made of materials which are approved for blood contact. Additionally, it is highly preferred that the entire assembly 10 be made of materials which are not heat-deformable in the range of commercial sterilization temperatures (approximately 230° to 250° F.) It is also desirable that the material of the thermoplastic member 20 be solvent bondable to medical grade polyvinyl chloride tubing 36 (shown in phantom lines in FIG. 3) to facilitate its attachment thereto, as well as be thermally bondable to the needle 18 in a manner which minimizes the chance of air leaks or gaps in the bond. Furthermore, the thermoplastic member 20 should be generally rigid to facilitate its insertion into the bore 26 of the elastomeric member 24.

With the above operative criteria in mind, a highly plasticized vinyl material can be utilized for the elastomeric member 24.

With regard to the thermoplastic member 20, the material selected for the member 20 should preferably thermally bond to stainless steel, because stainless steel is the most commonly utilized material for phlebotomy needles. Thus, polycarbonate and copolymers of acrylantrile, butadiene, and stryrene (ABS) can be utilized, because they are approved blood contact materials which are thermally bondable to stainless steel, autoclavable, and solvent bondable to polyvinyl chloride plastic.

However, in light of the high performance requirements surrounding cannula support assemblies, and the resulting need to maximize the bonding characteristics of the member 20 to the needle 18, it is thought to be highly desirable that a polyester material be utilized. This is because polyester materials are approved for blood contact and are solvent bondable to polyvinyl chloride plastics, and many, such as the amorphous copolyesters, exhibit superior bonding characteristics to stainless steel.

For example, and as discussed in the abovecited copending application entitled AN AUTOCLAVABLE THERMOPLASTIC MATERIAL WHICH IS HEAT BONDABLE TO A CANNULA AND THE LIKE, a poly(ethylene terephthalate)-based thermoplastic copolyester manufactured and sold by Eastman Chemical Products, Inc. as KODAR TM PETG Copolyester 6763 (hereafter PETG) is a highly rigid material which has superior bonding characteristics with stainless steel. PETG 6763 is an amorphous copolyester having a glass transition temperature of about 81° C. and a number average molecular weight of about 26,000. It has been observed that, after bonding a stainless steel needle to a PETG member, a pulling force in excess of 50 pounds must be exerted outwardly along the axis of the needle 18 to break the bond. This force will hereafter be identified as the "pull value" of the bond. Unfortunately, however, the PETG material melts at autoclaving temperatures and thereby does not meet one of the most desired operative criteria for the assembly 10.

There is a thermoplastic copolyetherester manufactured and sold by E. I. DuPont as HYTREL 4056 (hereafter HYTREL) which has a melting point in excess of 300° F. and, hence, does not melt at autoclaving temperatures. HYTREL is a thermoplastic copolyester elastomer having a melting point of about 168° C. The HYTREL material also does thermally bond to stainless steel, although not nearly as well as the PETG material, having an observed pull value (after autoclaving) of approximately 20 pounds. However, the elastomeric nature of the HYTREL material makes it unsuited for facile insertion within the elastomeric member 24.

It has been discovered that the lower thermal bonding characteristics and the lack of desired rigidity of the HYTREL material can be significantly overcome, without destroying the very desirable autoclavable character of the HYTREL material, by the addition of a predetermined amount of the PETG material.

More particularly, it has been determined that a mixture of approximately 60% by weight of the HYTREL material and approximately 40% by weight of the PETG material results in a generally rigid, autoclavable thermoplastic polyester material having an enhanced pull value (after autoclaving) which exceeds that of the HYTREL material alone (after autoclaving). Furthermore, the mixture thermally bonds to stainless steel without the appearance of air gaps or voids in the bond interface. The resulting bond is fluid-tight and uniformly secure.

The above-described mixture is thought to be optimal for the performance requirements of the illustrated embodiment. A mixture employing lesser amounts of the PETG material (less than approximately 30% PETG by weight) has been observed to exhibit a correspondingly lower pull value, whereas a mixture employing more amounts of the PETG material (more than approximately 50% PETG by weight) has been observed to be overly rigid and does not uniformly assure the same fluid-tight bonding characteristics, because of the appearance of air gaps or voids along the bond interface.

The above-described construction and materials enable an expedited and straightforward manufacturing process which lends itself to automated techniques, such as those utilizing an assembly line or an indexing turntable.

In the process, the thermoplastic member 20 and elastomeric member 24 are each individually fabricated (see FIG. 1). It should be noted that the tubular configuration of each of the members 20 and 24 lends itself to extrusion techniques, which lead to further economies, both in time and money. The preselection of polyester and vinyl materials, respectively, for the members 20 and 24 facilitate these economies, for both are extrudable materials.

In the next step in the process (see FIG. 2), the thermoplastic member 20 is inserted within the bore 26 of the elastomeric member 24. Due to the greater length of the thermoplastic member 20, opposite ends of the member 20 extend outwardly of the elastomeric member 24.

The needle 18 is next inserted into the bore 22 of the thermoplastic member 20. The slide-fit relationship afforded by the normal interior configuration of the bore 22 relative to the needle 18 greatly facilitates this step of the process.

Preferably, the elastomeric member 24 includes an axially extending exterior ridge or shoulder 34, relative to which the beveled end of the needle 18 is oriented (see FIG. 2). Proper bevel orientation is desirable, because it assures that the sharpest point of the needle 18 breaks the skin during venipuncture.

In the next step, and as is shown in phantom lines in FIG. 3, the needle 18 is heated, such as by utilizing the electromagnetic heating unit 28 shown in phantom lines. A heat conducting pin (not shown) may be inserted into the bore of the needle 18 to enhance the transmission of heat along the entire length of the needle 18, particularly if the needle 18 is made of a nonmetallic material. Alternately, the needle 18 may be heated by electrical resistance, heat induction, or any comparable method which focuses thermal energy along the needle 18. Utilizing this technique, the heat emanating from the needle quickly exceeds the temperatures normally encountered during commercial autoclaving procedures.

As before described, the thermoplastic member 20 softens and becomes deformable in the presence of the heat emanating from the needle 18. The force exerted by the surrounding elastomeric member 24 brings the softening thermoplastic member 20 into the desired conformance fit about the needle 18.

The finished assembly 10 can be subsequently sterilized by autoclaving and attached to the tubing 36 as a preassembled unit without disturbing the fluid-tight bond between the needle 18 and the assembly 10, and without disturbing the desired bevel orientation of the needle 18.

From the foregoing, it is clear that the assembly 10 not only facilitates a fast and efficient manufacturing process, but also results in a durable finished product which promotes a safe and comfortable venipuncture.

EXAMPLE 1

Utilizing the above described process, the thermoplastic member 20 comprising an extrusion of 60% by weight of the HYTREL material and 40% by weight of the PETG material and having an outside diameter of approximately 0.128 inch and a bore diameter of approximately 0.067 inch was inserted within the bore of the elastomeric member 24. The elastomeric member 24 was made of extruded vinyl having a 62 durameter measured on a Shore A durameter. The vinyl member 24 had a maximum outside diameter of approximately 0.325 inch and a bore diameter of approximately 0.12 inch. An approximate 0.008 interference fit was thus provided. The needle 18 was stainless steel and had a 16-gauge diameter (exterior diameter approximately 0.065 inch). An approximately difference of 0.002 inch between the exterior diameter of the needle 18 and the interior diameter of the thermoplastic member bore was thus provided. The exterior surface of the needle 18 had been sandblasted. After slip-fit insertion into the bore 22 of the thermoplastic member 20, the needle 18 was exposed for 1½ seconds to a 450 KHz frequency generated by a 300 watt induction generator through a copper coil having 5 turns and overall dimensions of 9/16th inch by 15/16th inch. After this 1½ second heating cycle, the fluid-tight, thermally bonded conformance fit between the thermoplastic member 20 and the needle 18 was observed to have a pull value (after autoclaving) of approximately 29 pounds.

EXAMPLE 2

The same materials employed in Example 1, except the needle 18 utilized was not sandblasted, were subjected to a heating cycle in which the needle 18 was exposed for a lesser period of time (0.8 second) to a 450 KHz frequency output of the same 300 watt induction generator, although this time the electromagnetic field was intensified by the use of a coil having 6½ turns and overall dimensions of ½ inch by 1 1/16th inches. After this shorter, more heat-intense cycle, the fluid-tight, thermally bonded conformance fit was observed to have an enhanced pull value (after autoclaving) of approximately 55 pounds.

EXAMPLE 3

The same materials utilized in Example 2 were subjected to a heating cycle in which the needle 18 was exposed for a lesser period of time (0.15 second) to an intensified electromagnetic field consisting of a 450 KHz frequency generated by a 2½ KW induction generator through a coil having 6 turns and overall dimensions of ⅝th by 1⅜th inches. The fluid-tight, thermally bonded conformance fit was observed to have an enhanced pull value (after autoclaving) of approximately 55 pounds.

The significantly increased pull value in Examples 2 and 3 (i.e., approximately 55 pounds), as compared to the pull value observed in Example 1 (i.e., approximately 29 pounds), despite the use of smooth (i.e., not sandblasted) needles, exemplifies the greater bonding strength resulting from the use of a shorter, but more heat-intense, cycle.

More particularly, inasmuch as the thermoplastic and elastomeric members 20 and 24 together act as a heat sink to carry away heat emanating from the needle 18 during the heating process, by maximizing the temperature of the needle 18 (by intensifying the electromagnetic field), the interior sidewall 30 of the thermoplastic member bore 22 is exposed to relatively higher temperatures. A better heat bond between the needle 12 and the thermoplastic member 20 along the interface of the bore sidewall 30 and needle 12 results.

Furthermore, by minimizing the overall time of this more heat-intense cycle, temperatures developed at more distance parts of the assembly 10 as the needle heat is dissipated by the above-described heat sink effect do not reach magnitudes sufficient to melt or otherwise structurally deform the remainder of the assembly 10.

An overall more durable and higher quality bond between the needle 18 and the assembly 10 results.

Furthermore, in order to optimize the durability and quality of the bond between the needle 18 and the assembly 10, it is preferred that the interference fit between the elastomeric member 20 and the thermoplastic member 22 (i.e., the difference between the interior diameter of the elastomeric member bore and exterior diameter of the thermoplastic member) be between approximately 0.004 inch and 0.012 inch, and that the difference between the exterior diameter of the needle 18 and interior diameter of the thermoplastic member bore be between approximately 0.001 inch and 0.004 inch.

It should be appreciated that the thermoplastic polyester material utilized for the member 22 is capable of uses in other contexts in which it is desirable to effect a durable and high quality bond with a metallic member.

Various of the features of the invention are set forth in the following claims.

I claim:

1. An autoclavable hub assembly for supporting a cannula comprising a first member made of a thermoplastic material consisting essentially of a combination of first and second polymers, said first polymer being present in an amount of from about 50% to about 70% by combined weight of said first and second polymers and being an autoclavable thermoplastic copolyester material, said second polymer being present in an amount of from about 30% to about 50% by combined weight of said first and second polymers and being a nonautoclavable amorphous thermoplastic copolyester material based on polyethylene terephthalate, said combination being autoclavable and bondable to the cannula in response to exposure to heat which emanates from the cannula and which exceeds the temperature sufficient to sterilize the cannula and said first member, said first member including an open interior having a normal configuration which, prior to said exposure to heat, slidingly receives the cannula and which, during said exposure to heat, is deformable about the cannula, and a second member made of an elastomeric material which is not heat deformable during said exposure to heat and which includes means for supporting said first member in an interference fit relationship within said second member and for deforming said first member during said exposure to heat to alter said normal configuration into a thermally bonded conformance fit configuration about the cannula.

2. An assembly according to claim 1
   wherein said autoclavable first polymer constitutes approximately 60% by combined weight of said first and second polymers, and
   wherein said nonautoclavable second polymer constitutes approximately 40% by combined weight of said first and second polymers.

3. An assembly according to claims 1 or 2
   wherein said second member includes an interior area having a determinable interior dimension and in which said first member is supported, and
   wherein said first member has an outside dimension which exceeds said interior dimension of said second member by between 0.004 inch and 0.012 inch.

4. An assembly according to claim 3
   wherein said first member has an interior dimension which exceeds the outside diameter of the cannula by between approximately 0.001 inch and 0.004 inch.

5. An assembly according to claim 1
   wherein said first polymer is a copolyetherester elastomer having a melting point of about 168° C.

6. An assembly according to claim 1 or 5
   wherein said second polymer is an amorphous copolyester having a glass transition temperature of about 81° C. and a number average molecular weight of about 26,000.

* * * * *